United States Patent
Watkinson

(10) Patent No.: US 7,771,527 B2
(45) Date of Patent: Aug. 10, 2010

(54) DENTAL FILLINGS AND BONE TISSUE

(76) Inventor: Charles Watkinson, Bridge Cottage, Long Lane, Great Heck, Yorkshire (GB) DN14 0BE ( * ) Notice: Subject to any disclaimer, the term of this patent is extended or adjusted under 35 U.S.C. 154(b) by 167 days.

(21) Appl. No.: 11/849,497

(22) Filed: Sep. 4, 2007

(65) Prior Publication Data

US 2008/0280747 A1 Nov. 13, 2008

(30) Foreign Application Priority Data

Sep. 2, 2006 (GB) .................................. 0617359

(51) Int. Cl.
*A61K 6/08* (2006.01)
*A61L 27/44* (2006.01)

(52) U.S. Cl. ................. 106/35; 106/690; 106/691; 523/113; 523/114; 523/115; 523/116; 523/117; 623/23.56; 623/23.61; 623/23.62; 623/23.58

(58) Field of Classification Search ............ 106/35, 106/691; 523/113–117; 623/23.56, 23.61, 623/23.62, 23.58; 433/228.1, 212.1, 201.1, 433/202.1

See application file for complete search history.

(56) References Cited

U.S. PATENT DOCUMENTS

| 5,017,207 A | 5/1991 | Watkinson et al. | |
|---|---|---|---|
| 2003/0162864 A1* | 8/2003 | Pearson et al. | 523/115 |
| 2006/0241205 A1* | 10/2006 | Jia | 523/115 |
| 2009/0088515 A1* | 4/2009 | Yagyu et al. | 524/494 |

FOREIGN PATENT DOCUMENTS

EP 0289240 A1 11/1988

* cited by examiner

*Primary Examiner*—C. Melissa Koslow
(74) *Attorney, Agent, or Firm*—Edwin D. Schindler

(57) ABSTRACT

A bone substitute composition includes glass flake and a hardenable material. The glass flake is a particle with an aspect ratio of, at least, 20:1. The preferred thickness of the glass flake is in the range from 200 to 1,000 nm and the average particle size is, preferably, from 20 to 60 μm.

5 Claims, No Drawings

DENTAL FILLINGS AND BONE TISSUE

BACKGROUND OF THE INVENTION

1. Technical Field of the Invention

This invention relates to polymeric and inorganic dental fillings, and bone tissue repair glues and compounds including sol-gels and, in particular, to compositions used to repair or augment teeth and bones in animals, including humans.

2. Description of the Prior Art

One of the problems with existing compositions for use as dental fillings or as repair or other compositions in bones generally is that they are subject to shrinkage on cure or hardening and high stress and fatigue levels over time.

European Patent Application No. 0,289,240 discloses a prior art procedure.

There is a need for more effective compositions, which are less subject to shrinkage and stress cracking even over long periods.

SUMMARY OF THE INVENTION

According to the present invention, there is provided a bone substitute composition comprising glass flake and a hardenable material.

By the term "bone substitute composition" is meant a material which may be used as a dental filling or a repair or augmenting composition for use with other bones. The overall composition of the material may vary from one application to another.

By the term "flake" is meant a particle with an aspect ratio of at least 20:1, that is to say, with the planar diameter being at least 20 times the thickness. The planar diameter is in practice the average particle size (D50) measured using a sieve mesh or by laser diffraction.

Preferably, the aspect ratio is from 50:1 to 1000:1, more preferably from 50:1 to 500:1 and most preferably from 50:1 to 300:1.

Preferably, the thickness of the glass flake is up to 1 μm. More preferably, the thickness of the glass flake is below 600 nm and can be as low as 50 nm.

Preferably, the average particle size of the glass flake ranges from 10 to 80 μm, in planar measurement, and 200 to 1000 nm in thickness. More preferably, the average particle size is from 20 to 60 μm in the planar direction and 100 to 400 nm in thickness. A particularly preferred glass flake is up to 50 μm in the planar direction and a thickness of around 350 nm is found to give particularly good properties including resistance to shrinkage.

DETAILED DESCRIPTION OF THE PREFERRED EMBODIMENTS

Glass flakes in accordance with the present invention may be made by a process similar to that described in European Patent Application No. 0,289,240. This method uses a spinning cup to produce a flat film of molten glass which is flung as a film in a radially outwards direction from the rim of the cup. The film is spread between two plates which form an annular venturi and is super-cooled with forced air. The film is broken up as a result of the high velocity air stream and the drag (frictional resistance) imparted by it.

The parameters involved in producing a flat glass flake of even thickness are varied and complex. These parameters and considerations include:

glass composition, melt temperature and viscosity;
temperature of glass in the melt tank;
mass flow of glass leaving the tank and entering the cup;
temperature of the glass entering the cup;
distance between the outlet of the glass tank and entry to the cup;
diameter and depth of the cup;
heat dissipation properties of the cup;
rotational speed of the cup;
distance between the rim of the cup and entry to the radial venturi;
distance of the plates forming the radial venturi;
diameter of the venturi plates;
volume and pressure flowing between the venturi plates;
temperature of the air flowing between the venturi plates; and,
diameter and construction of the cyclone collector.

By appropriate manipulation of these parameters glass flakes can be produced which are flat or wavy, of substantial variance in thickness or consistence of thickness, and which are large or small and cross-sectioned.

Particular parameters, the control of which has allowed glass flake of very low thickness, are the control of the glass stream from the control of the melt tank at higher temperatures, the ability to regulate the mass stream accurately, the ability to control the spinning of the molten film accurately and to stretch that film before it is super-cooled and broken into flake.

In particular, the production of a glass stream at a higher temperature than previously used with less mass flow and less heat loss from the stream is important. Furthermore, insulation of the spinning cup as opposed to cooling, and closer tolerances on the cup size and annular venturi, a higher velocity through the venturi and lower air pressure, are all important.

Particular values of ranges of parameters, which have been found to be useful in the production of very thin glass flake, are as follows:

mass flow between 0.4 and 5 kilos per minute;
glass temperature at control nozzle of from 1,050 to 1,500° C.;
glass temperature at spinning cup from 1,000 to 1,380° C.;
distance between melt tank control nozzle and entry to spinning cup of from 75 to 850 nm;
spinning cup diameter of from 20 to 100 mm OD;
spinning cup depth of from 15 to 80 mm;
spinning cup externally cooled, insulated or heated,
distance between edge of spinner and entry to annular venturi of from 10 to 275 mm;
the gap between plates forming the annular venturi of from 2 to 22 mm; and,
air pressure within the system of from 120 to 760 mm water gauge Glass flake can be obtained from Glassflake Limited, a British company, including glass flake of around nano-thickness.

While only several embodiments of the present invention have been shown and described, it will be obvious to those skilled in the art that many modifications may be made to the present invention without departing from the spirit and scope thereof.

What is claimed is:

1. A bone substitute composition, comprising:
   glass flake having a thickness of from 50 nm to 600 nm; and,
   a hardenable material.

2. The bone substitute composition according to claim 1, wherein said glass flake has an average particle size, in planar measurement, of from 10 to 80 μm.

3. The bone substitute composition according to claim 2, wherein said glass flake has a thickness of at least 200 nm.

4. The bone substitute composition according to claim 1, wherein said glass flake has a thickness of from 100 nm to 400 nm.

5. The bone substitute composition according to claim 4, wherein said glass flake has a thickness of approximately 350 nm.

* * * * *